US008471067B2

(12) United States Patent
Gilheany et al.

(10) Patent No.: US 8,471,067 B2
(45) Date of Patent: Jun. 25, 2013

(54) CHIRAL PHOSPHORUS COMPOUNDS

(75) Inventors: Declan Gilheany, Clonskeagh (IE); Shane B. Robinson, Middleton (IE); Enda Bergin, Castlepollard (IE); Denise M. Walsh, Clarehall (IE); Audrius Rimkus, Brig (CH); Eoin F. Clarke, Castaheany (IE); Brian G. Kelly, Blackrock (IE); Eoghan M. McGarrigle, Castlebar (IE); Colm P. O'Mahony, Grantstown Village (IE); Cormac T. O'Connor, Delgany (IE)

(73) Assignee: University College Dublin, Dublin (IE)

( * ) Notice: Subject to any disclaimer, the term of this patent is extended or adjusted under 35 U.S.C. 154(b) by 1543 days.

(21) Appl. No.: 11/628,037

(22) PCT Filed: Jun. 1, 2005

(86) PCT No.: PCT/IB2005/002079
§ 371 (c)(1),
(2), (4) Date: Feb. 4, 2008

(87) PCT Pub. No.: WO2005/118603
PCT Pub. Date: Dec. 15, 2005

(65) Prior Publication Data
US 2008/0255391 A1    Oct. 16, 2008

(30) Foreign Application Priority Data

Jun. 1, 2004 (GB) .................................. 0412189.3
Jan. 14, 2005 (GB) .................................. 0500797.6

(51) Int. Cl.
*C07F 9/02* (2006.01)
(52) U.S. Cl.
USPC ........................................................ 568/14
(58) Field of Classification Search
USPC ........................................................ 568/14
See application file for complete search history.

(56) References Cited

PUBLICATIONS

Downie, I.M.; Holmes, J.B.; Lee, J.B. Chemistry and Industry, London, 1966, pp. 900-901.
Table of Contents for Ojima, L, Ed., Catalytic Asymmetric Synthesis; 2nd. Edn., Wiley-VCH, 2000.
Table of Contents for Brunner, H.; Zettlmeier, W. Handbook of Enantioselective Catalysis, VCH, Weinheim, 1993.
Appel, Rolf, "Tertiary Posphane/Tetrachloromethane, a Versatile Reagent for Chlorination, Dehydration, and P-N linkage," *Agnew Chem. Internat. Ed. Engl.* (1975) vol. 14:12, pp. 801-811.
Appel, Rolf, et al., "Functional Group Conversions Using Phosphorus (III) Reagents and Polyhalogenoalkanes," in "*Organophosphorus Reagents in Organic Synthesis*," Ed. Cadogan, John I.G. Academic Press London (1979) Chapter 9, pp. 387-431.
Barry, Carey N., et al., "Triphenylphosphine-Tetrachloromethane Promoted Chlorination and Cyclodehydration of Simple Diols," *J. Org. Chem.* (1981) 46, pp. 3361-3364.
Brown, John M., et al., "The Nucleophilic Displacement Route to Homochiral Arylphosphine Oxides," *Tetrahedron* (1990) vol. 46: 13/14, pp. 4877-4886.
Carey, Joseph V., et al., "Preparation of Enantiomerically Pure Phosphine Oxides by Nucleophilic Displacement Chemistry Using Oxazaphospholidines," *J. Chem. Soc.*, Perkin. Trans. 1 (1993) pp. 831-839.
Castro, B. , et al., "Reaction du trichlorométhylure de trisdimethlaminiochloro phosponium sur las fonction carbonyle," *Bulletin De La Société Chimique De France* (1969) No. 8, pp. 2770-2773.
Castro, Bertrand, et al., "Préparation, stabilités, réactivité des sels de trisdiméthylamnio alcoyloxyphosphonium à alcoyle primaire," Bulletin De La Société Chimique De France (1971) No. 6, pp. 2296-2298.
Denney, Donald B., et al., "The Stereochemistry of Some Oxidations of Phenylmethylpropylphosphine," *Tetrahedron Letters* (1963) vol. 4:30, pp. 2177-2180.
Heinicke, Joachim, et al., "P/O Ligand Systems: Synthesis, Reactivity, and Structure of Tertiary o-Phospanylphenol Derivatives," *Chem. Ber.* (1996) 129, pp. 1547-1560.
Homer, L., "Darstellung Und Eigenschaften Optisch Aktiver, Tertiärer Phosphine," *Pure Appl. Chem.* (1964), vol. 9:2, pp. 225-244.
Kagan, Henri R., "Asymmetric Catalysis in Organic Synthesis with Industrial Perspectives," Bulletin De La Société Chimique De France (1988) No. 5, pp. 846-853.
Knowles, W. S., "Application of Organometallic Catalysis to the Commercial Production of $_L$-DOPA," *Journal of Chemical Education* (1986) vol. 63:3 pp. 222-225.
Kolodiazhnyi, Oleg I., "Stereoselective Oxidation of N-Phosphor (III) Substituted Amino Acids," *Tetrahedron Letters* (1995)vol. 36, No. 22 pp. 3921-3924.
Kolodiazhnyi, Oleg I., et al., "Diastereoselective Rearrangements and Epimerization of Organophoshorus Compounds," *Phosphorus, Sulfur, and Silicon* (1996) vol. 109-110 pp. 485-488.
Kolodiazhyni, Oleg I., "Asymmetric synthesis of organophosphorus compounds," *Tetrahedron: Asymmetry* 9 (1998) pp. 1279-1332.
Magid, Ronald M., et al., "Hexachloroacetone/Triphenylphosphine: A Mild Reagent for the Regioselective and Stereospecific Production of Allylic Chlorides from the Alcohols," *J. Org. Chem.* (1979) vol. 44: 3, pp. 359-363.
Mitsunobu, Oyo, "The Uses of Diethyl Azodicarboxylate and Triphenylphosphine in Synthesis and Transformation of Natural Products," *Synthesis* (1981) pp. 1-28. Miyake, Yoshihiro, et al., "Kinetic Resoluation of Racemic of Ferrocenylphosphine Compounds by Enantioselective Oxidation Using Cyclic Selenoxides Having a Chiral Ligand," *Bulletin of the Chemical Society of Japan* (2003) 76, pp. 381-387.

(Continued)

*Primary Examiner* — Peter G O Sullivan
(74) *Attorney, Agent, or Firm* — Steptoe & Johnson LLP

(57) ABSTRACT

A process for the stereoselective preparation of a P-chiral four-co-ordinated phosphorus compound, the process comprising reacting a first reactant selected from the group consisting of a chiral alcohol, chiral amine or chiral thiol, with a second reactant comprising a P-chiral three-co-ordinated phosphorus compound, in the presence of an electrophile.

54 Claims, No Drawings

PUBLICATIONS

Noyori, R. "Chemical Multiplication of Chiralty: Science and Applications," *Chem. Soc. Rev.* (1989) 18, pp. 187-208.

Perlikowska, Wieslawa, et al., "Kinetic resolution of P-chiral tertiary phosphines and chlorophosphines: a new approach to optically active phosphoryl and thiophosphoryl compounds," *Tetrahedron Letters* (2001) vol. 42, pp. 7841-7845.

Pietrusiewicz, K. Michal, et al., "Preparation of Scalemic P-Chiral Phosphines and Their Derivatives," *Chemical Review* (1994) 94, pp. 1375-1411.

Robinson, Philip L., et al., "Diethoxytriphenylphosporane: A Mild, Regioselective Cyclodehydrating Reagent for Conversion of Diols to Cyclic Ethers. Stereochemistry, Synthetic Utility, and Scope," *J. Am. Chem. Soc.* (1985) 107, pp. 5210-5219.

Downie, I. M., et al., "Preparation of Alkyl Chlorides Under Mild Conditions," *Chemistry and Industry* (1966) pp. 900-901.

Valentine, Donald, Jr., "Preparation of the Enantiomers of Compounds Containing Chiral Phosporus Centers," in *Asymmetric Synthesis*, eds. Morrison J. D. et al., Academic Press, New York, (1984) vol. 4, Chapter 3, pp. 263-312.

Villeneuve, G. B., et al., "A Rapid, Mild and Acid-Free Procedure for the Preparation of ACYL Chlorides Including Formyl Chloride," *Tetrahedron Letters* (1997) vol. 38: 37 pp. 6489-6492.

Appel, Rolf, "Tertiary Posphane/Tetrachloromethane, a Versatile Reagent for Chlorination, Dehydration, and P-N linkage," *Agnew Chem. Internat. Edit.* (1975) vol. 14:12, pp. 801-811.

Appel, Rolf, et al., "Functional Group Conversions Using Phosphorus (III) Reagents and Polyhalogenoalkanes," *Academic Press* (1979) Chapter 9, pp. 387-431.

Carey, Joseph V., et al., "Preparation of Enantiomerically Pure Phosphine Oxides by Nucleophilic Displacement Chemistry Using Oxazaphospholidines," *J. Chem. Soc.* (1993) pp. 831-839.

Denney, Donald B., et al., "The Stereochemistry of Some Oxidations of Phenylmethylpropylphosphine," *Pergamon Press Ltd* (1963) Petranedron Letters No. 30, pp. 2177-2180.

Horner, L., "Darstellung Und Eigenschaften Optisch Aktiver, Tertiärer Phosphine," *Eigenschaften Optisch Aktiver Tertiärer Phosphine* pp. 225-244.

Mitsunobu, Oyo, "The Uses of Diethyl Azodicarboxylate and Triphenylphosphine in Synthesis and Transformation of Natural Products," *Georg Thieme Verlag* (1981) pp. 1-28.

Miyake, Yoshihiro, et al., "Kinetic Resolution of Racemic of Ferrocenylphosphine Compounds by Enantioselective Oxidation Using Cyclic Selenoxides Having a Chiral Ligand," *The Chemical Society of Japan* (2003) 76, pp. 381-387.

Schweiger, Richard G., "Sodium Cellulose Sulphate," *Chemistry and Industry* (1966) pp. 900-901.

Valentine, Donald, Jr., "Preparation of the Enantiomers of Compounds Containing Chiral Phosporus Centers," *Associated Press* (1984) vol. 4, pp. 263-312.

Villeneuve, G. B., et al., "A Rapid, Mild and Acid-Free Procedure for the Preparation of ACYL Chlorides Including Formyl Chloride," *Tetrahedron Letters* (1997) vol. 38:37 pp. 6489-6492.

CHIRAL PHOSPHORUS COMPOUNDS

CLAIM OF PRIORITY

This application claims priority under 35 USC 371 to International Application No. PCT/IB2005/002079, filed on Jun. 1, 2005, which claims priority to British Patent Application No. 0412189.3, filed on Jun. 1, 2004 and British Patent Application No. 0500797.6, filed Jan. 14, 2005, each of which is incorporated by reference in its entirety.

FIELD OF THE INVENTION

The present invention relates to a process for preparing stereoisomerically enriched phosphorus containing compounds.

BACKGROUND TO THE INVENTION

The use of chiral non-racemic phosphorus compounds for catalytic asymmetric synthesis has grown enormously in the last three decades, such compounds providing many of the most successful ligands for metal-based catalysts (Ojima, 2000; Brunner et al., 1993).

Asymmetric reactions making use of metal catalysts with chiral phosphine ligands include alkene hydrogenations, hydroformylations and hydrosilylations, allylamine isomerisations, allylic substitutions and a number of cross coupling procedures. Some of these processes have gained industrial significance, e.g. Monsanto's L-dopa process (Knowles, 1986); Anic and Monsanto Aspartame process (Kagan, 1988) Syntex naproxen process (Noyori, 1989) and Takasago L-menthol process (Kagan, 1998). Chiral phosphorus compounds have been found to be useful non-metallic catalysts in their own right (Noyori, 1989).

Most of these catalysts involve the use of C-chiral, rather than P-chiral, phosphorus ligands, primarily because they are more easily prepared. However, P-chiral ligands can be of great value in catalytic asymmetric synthesis, as exemplified by the rhodium/diPAMP catalyst, developed by Knowles, which is one of the most successful catalysts used for the L-dopa and Aspartame syntheses.

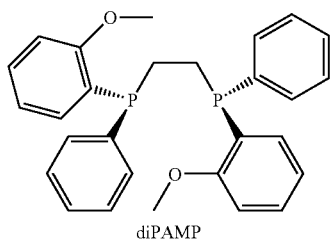 [SMILES: COc1ccccc1[P@@](CC[P@@](c1ccccc1)c1ccccc1OC)c1ccccc1]

diPAMP

In light of the beneficial properties of P-chiral phosphorus compounds in asymmetric synthesis, the search for efficient methods for the synthesis of P-chiral, non-racemic phosphines and related compounds such as phosphine oxides and phosphine sulfides continues to be of prime importance (Pietrusiewicz et al., 1994).

A number of strategies have been employed in the synthesis chiral phosphines. In principle, the most direct route to optically active phosphines is to resolve the racemic phosphine by making diastereomeric transition metal complexes. However, problems associated with the separation of the complexes, the synthesis of optically active ligands and the recycling of expensive metals have prevented this method from being generally applied. Another method used to resolve phosphorus compounds is the formation of phosphonium salts using a chiral counterion (Horner et al., 1964). However, this route has a number of limitations, especially in cleavage reactions of the resultant non-racemic salts where the stereochemical outcome cannot be guaranteed (Valentine, 1984).

The generation of chiral phosphines oxides from phosphinate esters has been widely used (Valentine, 1984), but the success of this method heavily depends on the availability of chiral phosphinate esters, and much effort has been expended in the search for methods to generate these esters, with only limited success. Likewise, the synthesis of chiral phosphines by the electrophilic substitution of chiral phosphonites (Valentine, 1984) is hindered by the availability of suitable phosphonites, which have low optical stability compared with phosphines.

Reduction of chiral four coordinated phosphorus compounds such as phosphine oxides is perhaps the most common route to chiral phosphines and can be achieved by a number of reagents including hydrides, boranes and silanes, the choice of which is determined by the sensitivity of the compound to reduction and the stereochemistry required in the product phosphine. At present, the preferred reductants for phosphine oxides are silanes. However, the use of such reduction methods has merely pushed the stereoselectivity problem back to an earlier stage in the synthesis, i.e. a source of a chiral four-co-ordinated phosphorus compound is now required, such as a chiral phosphine oxide. The synthesis of enantiomerically enriched phosphine oxides and phosphine sulfides based on the kinetic resolution of P-chiral three-coordinate phosphorus compounds using pure bis-phosphoryl or bis-thiophosphoryl disulfides is discussed in Perlikowska et al, 2001.

There remains a clear need for methods of preparing P-chiral four-co-ordinated phosphorus compounds. Such compounds can be converted into the corresponding P-chiral three-coordinated phosphorus compounds by reduction and have important uses in pharmaceutical and agrochemical applications in their own right.

STATEMENTS OF THE INVENTION

According to a first aspect of the present invention there is provided a process for the stereoselective preparation of a P-chiral four-co-ordinated phosphorus compound, the process comprising reacting a first reactant selected from the group consisting of a chiral alcohol, chiral amine or chiral thiol, with a second reactant comprising a P-chiral three-co-ordinated phosphorus compound in the presence of an electrophile.

According to another aspect of the present invention there is provided a process for the stereoselective preparation of a P-chiral four-co-ordinated phosphorus compound, the process comprising reacting a first reactant selected from the group consisting of a chiral alcohol, chiral amine or chiral thiol, with a second reactant comprising a P-chiral three-co-ordinated phosphorus compound, in the presence of an electrophile, and isolating said P-chiral four-co-ordinated phosphorus compound.

According to another aspect of the present invention there is provided a process for the stereoselective preparation of a P-chiral three-co-ordinated phosphorus compound, the process comprising the steps of:
(i) stereoselectively preparing a P-chiral four-co-ordinated phosphorus compound, said preparation comprising reacting a first reactant selected from the group consisting of a chiral alcohol, chiral amine or chiral thiol, with a second reactant comprising a P-chiral three-co-ordinated phosphorus compound, in the presence of an electrophile;

(ii) optionally isolating said P-chiral four-co-ordinated phosphorus compound; and (iii) reducing said P-chiral four-co-ordinated phosphorus compound to a P-chiral three-co-ordinated phosphorus compound.

In one embodiment, the aforementioned process is repeated more than once in order to improve the enantiomeric excess (ee) of the product P-chiral three-co-ordinated phosphorus compound. That is to say, the product P-chiral three-co-ordinated phosphorus compound obtained in step (iii) is used in step (i).

Preferably the second reactant comprising a P-chiral three-co-ordinated phosphorus compound is racemic. However, the process of the present invention can be used to stereoselectively prepare P-chiral four-co-ordinated phosphorus compounds and P-chiral three-co-ordinated phosphorus compound derived therefrom starting from a P-chiral three-co-ordinated phosphorus compound that does not comprise enantiomers in equal concentration.

The second reactant consisting of a P-chiral three-co-ordinated phosphorus compound may also comprise a mixture of diastereoisomers which may or may not be in equal concentration.

The P-chiral four-co-ordinated phosphorus compound prepared by the present invention may be a phosphine oxide, a phosphine sulfide, or an aminophosphonium salt. The sulfur, oxygen and nitrogen atom of the phosphine sulfide, phosphine oxide, and aminophosphonium salt is donated by the chiral thiol, chiral alcohol and chiral amine respectively.

Preferably said chiral alcohol, chiral thiol, and chiral amine are substantially homochiral, preferably having greater than 90% ee, more preferably greater than 95% ee, more preferably greater than 99% ee.

In a preferred embodiment, said P-chiral four-co-ordinated phosphorus compound is a phosphine oxide and said first reactant is a chiral alcohol.

In one embodiment the chiral alcohol has the formula:

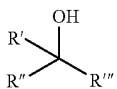

wherein R', R", and R'" are each independently hydrogen or hydrocarbyl with the proviso that R', R", and R'" cannot be identical.

In a preferred embodiment, two of R', R", and R'" together with the carbon atom bearing the hydroxyl group form a carbocyclic or heterocycloalkyl ring system.

In one embodiment the alcohol is a mono-alcohol, that is it contains one OH group.

Preferably, the chiral alcohol comprises a chiral centre that resides on the hydroxy carbon.

Preferably, the alcohol is a cyclic alcohol.

In one embodiment the chiral alcohol is a secondary or tertiary alcohol.

In one embodiment the chiral alcohol is a primary alcohol.

In one embodiment the chiral alcohol is a diol.

In one embodiment, the chiral alcohol used in the present invention is selected from the group comprising (−)-menthol, (−)-8-phenylmenthol, (−)-trans-2-tert-butylcyclohexanol, (+)-neomenthol, (+)-isomenthol, (S)-1-Octyn-3-ol, (R)-3-methyl-2-butanol, (S)-1-phenyl-1-butanol, (1R,2R)-2-benzoylcyclohexanol, isopinocampheol, cholesterol, (1S,2S,5R)-2-isopropyl-1,5-dimethylcyclohexanol, (−)-10-dicyclohexylsulfamoyl-D-isoborneol, (−)-trans-2-phenylcyclohexanol, (+)-fenchyl alcohol, (−)-benzenesulfonyl-N-(3,5-dimethylphenyl)amino-2-borneol, a fructose derivative including but not limited to 1,2:4,5-Di-O-isopropylidene-D-fructopyranoside, cyclohexandiol, (S)-(−)-2-amino-1,1-diphenyl propanol, (S)-(−)-2-amino-1,1-diphenyl propanol, (S)-(−)-2-amino-3-methyl-1,1-diphenyl-butan-1-ol, (R)-(+)-2-amino-(1,1,3)-triphenyl-propan-1-ol, (S)-(−)-2-amino-4-methyl-1,1-diphenyl-pentan-1-ol, (−)-trans-2-phenylcyclohexanol, diacetone-D-glucose and (−)-1,2-dicyclohexyl-1,2-ethanediol, or the corresponding enantiomers thereof.

In one embodiment said first reactant is a chiral amine.

Preferably the chiral amine has the formula:

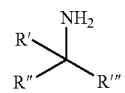

wherein R', R", and R'" are each independently hydrogen or hydrocarbyl with the proviso that R', R", and R'" cannot be identical.

In a preferred embodiment, two of R', R", and R'" together with the carbon atom bearing the hydroxyl group form a carbocyclic or heterocycloalkyl ring system.

In one embodiment said first reactant is a chiral thiol

In one embodiment the chiral thiol has the formula:

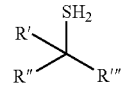

wherein R', R", and R'" are each independently hydrogen or hydrocarbyl with the proviso that R', R", and R'" cannot be identical.

In a preferred embodiment, two of R', R", and R'" together with the carbon atom bearing the thiol group form a carbocyclic or heterocycloalkyl system.

In one embodiment, the chiral thiol used in the present invention is (+)-neomenthane thiol.

Preferably, the second reactant P-chiral three-co-ordinated phosphorus compound used in the present invention has the formula:

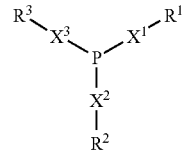

wherein $X^1$, $X^2$ and $X^3$ are each independently —$NR^5$ or absent; and wherein $R^1$, $R^2$, $R^3$ and $R^5$ are each independently hydrogen, halogen, hydrocarbyl or an organometallic group.

In one embodiment $X^1$, $X^2$ and $X^3$ are absent.

In another embodiment $X^1$, $X^2$ are absent and $X^3$ is present.

Preferably $R^1$, $R^2$, $R^3$ and $R^5$ are each independently an aryl, heteroaryl, alkyl, carbocycle, heterocycloalkyl, aralkyl (aryl-alkyl) or alkenyl group.

Preferably, $R^5$ is an alkyl group.

In one embodiment, the P-chiral three-co-ordinated phosphorus compound used in the present invention is as defined in Table 9.

Preferably the stereoselective preparation of the P-chiral four-co-ordinated phosphorus compound occurs in the presence of an electrophile that allows for the formation of a quaternary phosphonium salt and acts as a hydrogen acceptor.

In one embodiment the electrophile is a haloalkane.

Preferably the electrophile is selected from the group comprising, hexahaloacetone, hexahaloethane and N-halosuccinimide or $CX_4$, wherein X is a halogen. Preferably the halo component is a chlorine or bromine atom. More preferably the halo component is a chlorine atom.

In one embodiment the electrophile is selected form the group comprising carbon tetrachloride, hexachloroacetone, hexachloroethane, N-chlorosuccinimide, 2,3,4,5,6,6-hexachloro-2,4-cyclohexadiene-1-one and trichloroacetonitrile.

Preferred electrophiles for tertiary non-aminophosphines (i.e., when $X^1$, $X^2$ and $X^3$ are absent) are hexachloroacetone and N-chlorosuccinimide. A particularly preferred solvent is hexachloroacetone.

A particularly preferred electrophile for aminophosphines (i.e., when $X^1$, $X^2$ and/or $X^3$ are present) is carbon tetrachloride.

In one embodiment the electrophile is peroxide or disulfide, preferably diethylperoxide or bis(2-pyridyl)sulfide.

In another embodiment the process of the present invention is performed under Appel, Castro or Evans conditions or a modification thereof.

In one embodiment the process of the present invention may be carried out in a solvent.

The solvent is preferably aprotic. More preferably, the solvent is a non-polar solvent.

Preferably the solvent is an organic solvent, such as benzene, toluene, acetonitrile, diethyl ether, THF, dichloromethane, hexane, chloroform and carbon tetrachloride.

Preferably the solvent is selected from toluene, dichloromethane and THF. A particularly preferred solvent is toluene.

The process of the present invention may use one or more additives.

In one embodiment, the additive is a basic entity, such as, an inorganic or organic base. The base may be a basic alkaline or alkaline earth metal salt. Examples of such bases include, but are not limited to potassium carbonate and pyridine.

In one embodiment the additive is a metal salt such as a Lewis acid.

The chiral P-chiral four-co-ordinated phosphorus compound produced by the present invention may subsequently be converted to a dimeric form creating a mixture of scalemic and meso compounds. The scalemic compound is thereby produced in higher ee than the starting mono form—this is a consequence of the statistical nature of the dimerisation, it depletes the minor enantiomer. The scalemic compounds are then separated from the meso compounds by, for example, recrystallisation.

Preferably, the dimerisation occurs at an alkyl group, preferably a methyl group, attached to the phosphorous atom.

Preferably the scalemic chiral P-chiral four-co-ordinated phosphorus compound is o-Tolylphenylmethylphosphine oxide (PTMPO) and the corresponding dimer is 1,2-bis(phenylo-tolylphosphinoyl)ethane (diPTMPO).

Preferably the scalemic chiral P-chiral four-co-ordinated phosphorus compound is o-anisylmethylphenylphosphine (PAMPO) and the corresponding dimer is 1,2-bis(phenyl(2-methoxyphenyl)phosphinoyl)ethane (diPAMPO, also known as ethane-1,2-diylbis[(2-methoxyphenyl)phenylphosphane], P,P'-bisoxide).

In another embodiment, the dimer is reduced to generate the corresponding bis-phosphine. For example, the dimer may be reduced to generate diPTMP, also known as 1,2-bis(phenyl(2-methylphenyl)phosphino)ethane (or ethane-1,2-diylbis[(2-methylphenyl)phenylphosphane]) or diPAMP (also known as ethane-1,2-diylbis[(2-methoxyphenyl)phenylphosphane]).

The process of the present invention may have an initiation phase and a reaction phase. In a preferred embodiment, low temperature initiation is used, wherein the reaction mixture is initially cooled to below room temperature. Preferably, the reaction mixture is cooled below 0° C., more preferably below −30° C., more preferably below −50° C., still more preferably below −70° C. In a preferred embodiment, the reaction is cooled to about −78° C. This is particularly beneficial for tertiary, non-aminophosphines (wherein $X^1$, $X^2$ and/or $X^3$ are absent).

The reaction phase may take place at, for example, at room temperature or at reflux.

After initiation and warming to room temperature, raising the temperature to 50-60° C. for a period of time (30-60 minutes) can be beneficial. This is because it finishes the reaction and does not affect the selection.

A skilled person will appreciate that the best temperature for the initiation and reaction phase depends on the alcohol, amine or thiol used.

Preferably, room temperature initiation is used for aminophosphines (wherein $X^1$, $X^2$ and/or $X^3$ are present).

As the skilled person will appreciate, the process of the present invention may, in addition to three and four co-ordinated phosphorus compounds, produce other products of commercial value. Such products include chiral alkyl halides derived from the first reactant and chiral epoxides produced, for example, when the chiral alcohol is a 1,2-diol.

Some of the products of the present process are ideal branch points for the synthesis of a large number of other P-chirogenic phosphorus compounds. Thus, for example, those that carry a methyl group attached to phosphorus can be deprotonated at the methyl group with suitable base and subsequently treated with a wide variety of electrophiles. In this way, a modular approach can be envisaged for the generation of libraries of useful phosphorus compounds.

DETAILED DESCRIPTION

The present invention is based on the finding that P-chiral four-co-ordinated phosphorus compounds can be stereoselectively prepared by reacting a chiral alcohol, chiral amine or chiral thiol with a P-chiral three-co-ordinated phosphorus compound in the presence of an electrophile.

The term stereoselective preparation refers to a preparation that yields predominantly one entantiomer or one diastereomer. Preferably the ee is greater than 25%, more preferably greater than 30%, more preferably greater than 50%, more preferably greater than 60%, more preferably greater than 70%, more preferably greater than 80%. Stereoselective reactions can be of two types: enantioselective, in which selection is between two enantiomeric products; and diastereoselective, in which selection is between diastereomeric products.

The term P-chiral refers to a phosphorus containing compound wherein a chiral centre resides on the phosphorus atom.

In one embodiment the process of the present invention uses an Appel, Castro or Evans type reaction. A skilled person would readily appreciate that modifications of these well known reactions also fall within the scope of the present invention.

The Appel reaction is based on a reaction system comprising a three-coordinated phosphine compound and polyhalogenoalkanes such as carbon tetrachloride (Appel et al., 1979; Appel, 1975). The first report of the use of a mixture of triphenylphosphine and carbon tetrachloride to effect the conversion of alcohols to alkyl halides (one of the best known uses of the most common version of the Appel system) was by Downie, Holmes and Lee in 1966 (Downie et al., 1966).

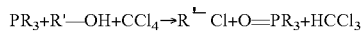

EXAMPLE OF AN APPEL REACTION

The halogen group of the electrophile acts as an electrophile, associating with the phosphine to form a quaternary phosphonium salt which then undergoes nucleophilic attack. The specific system based on tris(dimethylamino)phosphine was studied in the late 60s and early 70s by Castro and co-workers (Castro et al., 1969; Castro et al., 1971) and his name is sometimes associated with this variant of Appel. Related systems for the conversion, amongst others, of diols to cyclic ethers, were reported by Evans (Barry et al., 1981; Robinson et al., 1985). As well as its most significant conversions, namely conversion of alcohols to alkyl halides and ester and amide formation, these systems are useful for an extremely wide variety of other organic chemical transformations (Kolodiazhnyi, 1998; Appel, 1975; Cadogan, 1979) including the preparation of 1,1-dichloroalkenes from aldehydes, ketones and epoxides; acid halides from the parent acid; imidoyl halides from carboxamides and carbodiimides from N,N'-disubstituted ureas.

In all of the reactions promoted by Appel, Castro and Evans, conditions, the ultimate function of the phosphorus species is to collect a Group 15 or 16 atom (for example, an oxygen, sulfur or nitrogen atom) from the system. In the formation of alkyl halides from alcohols, for example, the oxygen of the alcohol ends up attached to the phosphorus atom.

In these reactions the formation of the e.g., phosphine oxide or sulphide is seen as a by-product of the process. Indeed, it can be a nuisance in certain cases if it cannot be easily removed from the desired product of the reaction.

In this work we focus on the four-co-ordinate phosphorus "by-product" and have found that the above systems are useful for the stereoselective preparation of P-chiral four co-ordinate phosphorus compounds.

The process of the present invention is intended to prepare P-chiral phosphine oxides and other such P-chiral four-coordinated phosphorus compounds, and three-coordinate P-chiral phosphorus compounds derived from these.

Thus, according to one aspect of the present invention there is provided a process for the stereoselective preparation of a P-chiral three-co-ordinated phosphorus compound, the process comprising the steps of:
  (i) stereoselectively preparing a P-chiral four-co-ordinated phosphorus compound, said preparation comprising reacting a first reactant selected from the group consisting of a chiral alcohol, chiral amine or chiral thiol, with a second reactant comprising a P-chiral three-co-ordinated phosphorus compound, in the presence of an electrophile;
  (ii) optionally isolating said P-chiral four-co-ordinated phosphorus compound; and
  (iii) reducing said P-chiral four-co-ordinated phosphorus compound.

Reduction of the P-chiral four-co-ordinated phosphorus compound can be achieved by a number of reagents that are well known in the art including hydrides, boranes and silanes, the choice of which is determined by the sensitivity of the oxide to reduction and the stereochemistry required in the product P-chiral three-co-ordinated phosphorus compound. Examples of such reduction methods can be found, for example, in Louis D Quin, A Guide to Organophosphorus Chemistry, John Wiley & Sons, 2000.

As used herein, the term alcohol refers to any organic molecule comprising at least one hydroxy group bonded to a carbon atom.

The P-chiral compounds of the present invention (three or four co-ordinated) may, in addition, be chiral at least one other site, for example, another phosphorus atom and/or another carbon atom.

The starting material is a P-chiral three-co-ordinated phosphorus compound, such as a compound of the structural formula:

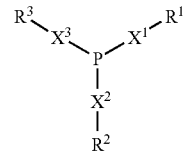

wherein $X^1$, $X^2$ and $X^3$ are each independently absent or —$NR^5$; and
wherein $R^1$, $R^2$, $R^3$ and $R^5$ may be any inorganic or organic moiety.

Preferably $R^1$, $R^2$, $R^3$ and $R^5$ are each independently hydrogen, halogen, hydrocarbyl or an organometallic group.

In one embodiment $R^1$, $R^2$, $R^3$ and $R^5$ are each independently an aryl, heteroaryl, alkyl, carbocycle, heterocycloalkyl, aralkyl, or alkenyl group.

Preferably $R^5$ is hydrogen, halogen or alkyl.

As used herein, the term "hydrocarbyl" refers to a group comprising at least C and H. If the hydrocarbyl group comprises more than one C then those carbons need not necessarily be linked to each other. For example, at least two of the carbons may be linked via a suitable element or group. Thus, the hydrocarbyl group may contain heteroatoms. Suitable heteroatoms will be apparent to those skilled in the art and include, for instance, sulphur, nitrogen, oxygen, phosphorus and silicon. Preferably, the hydrocarbyl group is an aryl, heteroaryl, alkyl, carbocycle, heterocycloalkyl, aralkyl or alkenyl group.

As used herein, the term "alkyl" includes both saturated straight chain and branched alkyl groups which may be substituted (mono- or poly-, preferably 1 to 3 substituents, more preferably one substituent) or unsubstituted. In one embodiment the alkyl group is a $C_{1-20}$ alkyl group. In another embodiment the alkyl group is a $C_{1-15}$. In another embodiment the alkyl group is a $C_{1-12}$ alkyl group. In another embodiment the alkyl group is a $C_{1-6}$ alkyl group. Suitable substituents include, for example, a group selected from halogeno, $NO_2$, CN, $(CH_2)_m OR^a$, where m is 0, 1, 2 or 3, $O(CH_2)_n OR^b$, where n is 1, 2, or 3, $NR^c R^d$, $CF_3$, $COOR^e$, $CONR^f R^g$, $COR^h$, $SO_3H$, $SO_2 R^i$, $SO_2 NR^j R^k$, heterocycloalkyl or heteroaryl, wherein said heterocycloalkyl and heteroaryl may be optionally substituted by one or more substituents selected from $R^m$ and $COR^n$; and $R^{a-n}$ are each independently H or alkyl.

As used herein, the term "carbocycle" refers to a mono- or multi-ringed carbocyclic ring system which may be substituted (mono- or poly-, (mono- or poly-, preferably 1 to 3 substituents, more preferably one substituents)) or unsubstituted. Preferably the multi-ringed carbocycle is bi- or tricyclic. Preferably the carbocycle is a $C_{3-20}$ carbocyclic group. More preferably the carbocycle is a $C_{3-12}$ carbocyclic group. More preferably the carbocycle group is a $C_{3-7}$ carbocyclic group. Suitable substituents include, for example, a group selected from halogeno, $NO_2$, CN, $(CH_2)_mOR^a$, where m is 0, 1, 2 or 3, $O(CH_2)_nOR^b$, where n is 1, 2, or 3, $NR^cR^d$, $CF_3$, $COOR^e$, $CONR^fR^g$, $COR^h$, $SO_3H$, $SO_2R_i$, $SO_2NR^jR^k$, heterocycloalkyl or heteroaryl, wherein said heterocycloalkyl and heteroaryl may be optionally substituted by one or more substituents selected from $R^m$ and $COR^n$; and $R^{a-n}$ are each independently H or alkyl. Preferably the substituents are selected from halogeno, $(CH_2)_mOR^a$, where m is 0, 1, 2 or 3, $NR^cR^d$, $COOR^e$, $CONR^fR^g$, $COR^h$. Preferably the carbocycle is a carbocycle ring. Preferably the carbocycle is a cycloalkyl.

As used herein, the term "cycloalkyl" refers to a mono- or multi-ringed cyclic alkyl group which may be substituted (mono- or poly-, preferably 1 to 3 substituents, more preferably one substituent)) or unsubstituted. Preferably the multi-ringed cyclic alkyl group is bi- or tri-ringed. Preferably the cycloalkyl group is a $C_{3-20}$ cycloalkyl group. More preferably the cycloalkyl group is a $C_{3-12}$ cycloalkyl group. More preferably the cycloalkyl group is a $C_{3-7}$ cycloalkyl group. Suitable substituents include, for example, a group selected from halogeno, $NO_2$, CN, $(CH_2)_mOR^a$, where m is 0, 1, 2 or 3, $O(CH_2)_nOR^b$, where n is 1, 2, or 3, $NR^cR^d$, $CF_3$, $COOR^e$, $CONR^fR^g$, $COR^h$, $SO_3H$, $SO_2R_i$, $SO_2NR^jR^k$, heterocycloalkyl or heteroaryl, wherein said heterocycloalkyl and heteroaryl may be optionally substituted by one or more substituents selected from $R^m$ and $COR^n$; and $R^{a-n}$ are each independently H or alkyl. Preferably the substituents are selected from halogeno, $(CH_2)_mOR^a$, where m is 0, 1, 2 or 3, $NR^cR^d$, $COOR^e$, $CONR^fR^g$, $COR^h$.

As used herein the term "heterocycloalkyl" refers to a cycloalkyl group containing one or more heteroatoms selected from O, N and S. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, pyrrolidinyl, dihydrofuranyl, tetrahydropyranyl, pyranyl, thiopyranyl, aziridinyl, oxiranyl, methylenedioxyl, chromenyl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, thiomorpholinyl, 1,2-tetrahydrothiazin-2-yl, 1,3-tetrahydrothiazin-3-yl, tetrahydrothiadiazinyl, 1,2-tetrahydrodiazin-2-yl, 1,3-tetrahydrodiazin-1-yl, tetrahydroazepinyl, piperazinyl, chromanyl, etc. Additionally, for heterocycloalkyl, a heteroatom can occupy the position at which the heterocycle is attached to the remainder of the molecule. Thus, one of ordinary skill in the art will understand that the connection of said heterocycloalkyl rings is through a carbon or a $sp^3$ hybridized nitrogen heteroatom. Preferred heterocycloalkyl groups include piperazine, morpholine, piperidine and pyrrolidine.

As used herein, the term "alkenyl" refers to a group containing one or more carbon-carbon double bonds, which may be branched or unbranched, substituted (mono- or poly-, preferably 1 to 3 substituents, more preferably one substituent) or unsubstituted. In one embodiment the alkenyl group is a $C_{2-20}$ alkenyl group. In another embodiment the alkenyl group is a $C_{2-15}$ alkenyl group. In another embodiment the alkenyl group is a $C_{2-12}$ alkenyl group. In another embodiment the alkenyl group is a $C_{2-6}$ alkenyl group. Suitable substituents include, for example, a group selected from halogeno, $NO_2$, CN, $(CH_2)_mOR^a$, where m is 0, 1, 2 or 3, $O(CH_2)_nOR^b$, where n is 1, 2, or 3, $NR^cR^d$, $CF_3$, $COOR^e$, $CONR^fR^g$, $COR^h$, $SO_3H$, $SO_2R^i$, $SO_2NR^jR^k$, heterocycloalkyl or heteroaryl, wherein said heterocycloalkyl and heteroaryl may be optionally substituted by one or more substituents selected from $R^m$ and $COR^n$; and $R^{a-n}$ are each independently H or alkyl. Preferably the substituents are selected from halogeno, $(CH_2)_mOR^a$, where m is 0, 1, 2 or 3, $NR^cR^d$, $COOR^e$, $CONR^fR^g$, $COR^h$.

As used herein, the term "aryl" refers to a mono- or multi-ringed aromatic group which may be substituted (mono- or poly-, preferably 1 to 3 substituents, more preferably one substituent) or unsubstituted. Preferably the multi-ringed aromatic group is bi- or tri-ringed. Preferably the aromatic group is a $C_{5-20}$ aryl group. More preferably the aryl group is a $C_{6-12}$ aromatic group. Typical examples include phenyl and naphthyl etc. Suitable substituents include, for example, a group selected from halogeno, $NO_2$, CN, $(CH_2)_mOR^a$, where m is 0, 1, 2 or 3, $O(CH_2)_nOR^b$, where n is 1, 2, or 3, $NR^cR^d$, $CF_3$, $COOR^e$, $CONR^fR^g$, $COR^h$, $SO_3H$, $SO_2R_i$, $SO_2NR^jR^k$, heterocycloalkyl, aryl or heteroaryl, wherein said heterocycloalkyl and heteroaryl may be optionally substituted by one or more substituents selected from $R^m$ and $COR^n$; and $R^{a-n}$ are each independently H or alkyl. Preferably the substituents are selected from halogeno, $(CH_2)_mOR^a$, where m is 0, 1, 2 or 3, $NR^cR^d$, $COOR^e$, $CONR^fR^g$, $COR^h$.

As used herein, the term "heteroaryl" refers to a $C_{4-12}$ aromatic, substituted (mono- or poly-, preferably 1 to 3 substituents, more preferably one substituent) or unsubstituted group, which comprises one or more heteroatoms, preferably 1 to 3 heteroatoms, more preferably one heteroatom, independently selected from N, O and S. Preferably the heteroatom is N or S. Preferred heteroaryl groups include pyrrole, pyrazole, pyrimidine, pyrazine, pyridine, quinoline, triazole, tetrazole, thiophene, furan imidazole and oxazolidine. Suitable substituents include, for example, a group selected from halogeno, $NO_2$, CN, $(CH_2)_mOR^a$, where m is 0, 1, 2 or 3, $O(CH_2)_nOR^b$, where n is 1, 2, or 3, $NR^cR^d$, $CF_3$, $COOR^e$, $CONR^fR^g$, $COR^h$, $SO_3H$, $SO_2R^i$, $SO_2NR^jR^k$, heterocycloalkyl or heteroaryl, wherein said heterocycloalkyl and heteroaryl may be optionally substituted by one or more substituents selected from $R^m$ and $COR^n$; and $R^{a-n}$ are each independently H or alkyl. Preferably the substituents are selected from halogeno, $(CH_2)_mOR^a$, where m is 0, 1, 2 or 3, $NR^cR^d$, $COOR^e$, $CONR^fR^g$, $COR^h$.

The term cyclic alcohol, as used herein to define a group or a part of a group, unless otherwise stated, refers to a saturated or unsaturated mono or multi-ringed cyclic group containing from 3 to 20 carbon atoms, preferably 3 to 12 carbon atoms, more preferably 3-7 carbon atoms, substituted by at least one hydroxyl group and optionally substituted by one or more substituents. Suitable substituents include aryl, heteroaryl, alkyl, carbocycle, heterocycloalkyl, aralkyl and alkenyl groups. Preferably, the cyclic alcohol is substituted by 1 to 3 substituents, more preferably one or two substituents. Preferably the mono or multi-ringed cyclic group is saturated. Preferably the multi-ringed group is tricyclic or bicyclic. The stereoselectivity of the reaction is generally improved if the alcohol has a bulky substituent at the α position relative to the —OH. In one embodiment, the bulky substituent has 3 to 20 carbon atoms, preferably 3 to 12 carbon atoms, more preferably 3 to 9 carbon atoms. Examples of such bulky substituents include phenyl and isopropyl, cyclohexanol and dimethyl benzyl.

Examples of suitable cyclic alcohols include menthol, 8-phenylmenthol, trans-2-tert-butylcyclohexanol, isomenthol, 2-benzoylcyclohexanol and trans-2-phenylcyclohexanol.

Preferred organometallic groups are selected from the group consisting of ferrocenyl, ruthenacenyl, (bisindenyl)titanyl, (bisindenyl)zirconyl, (bisindenyl)hafnyl, (bisindenyl)niobyl, (bisindenyl)tantalyl, (bisindenyl)molybdenyl, and (bisindenyl)tungstenyl.

When $R^1$, $R^2$, $R^3$ or $R^4$ is an aralkyl group, the phosphorus or nitrogen may be directly bonded to either the alkyl component or the aryl component of said aralkyl group.

The P-chiral phosphorus compounds so prepared are four-coordinated phosphorus compounds such as phosphine oxides, phosphine sulfides and aminophosphonium salts. These compounds include compounds of the formula:

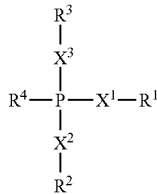

wherein $X^1$, $X^2$ and $X^3$ are each independently absent or —$NR^5$ as described above; and
wherein $R^1$, $R^2$, $R^3$ and $R^5$ may be any inorganic or organic moiety as described above; and wherein $R^4$ comprises, or includes, a sulfur, oxygen or nitrogen atom directly bonded to the phosphorus atom. Preferably, $R^4$ is an oxygen atom.

In the above structural formula, no charge is depicted. For the case where $R^4$ for example, comprises a single oxygen or sulfur atom, one skilled in the art would immediately appreciate that the phosphorus has a positive charge associated therewith and the $R^4$ a negative charge. Equally, in that case, the bond between the phosphorus and $R^4$ could be depicted as a double bond. For the case where $R^4$ for example comprises a group attached by a nitrogen atom one skilled in the art would immediately appreciate that the phosphorus has a positive charge associated therewith and that there is also a suitable counterion present.

Two intermediates are produced in the reaction of the present invention. The first is formed rapidly and decays rapidly to the second, over a period of seconds to minutes. The second is long-lived, from one hour up to 2 weeks, eventually converting fully to the product phosphine oxide. Selection may occur in either of the first two steps, i.e. those leading to the first and second intermediate.

The selection is commonly fixed when the second intermediate is formed. However in certain cases selection may be eroded with time and this is very noticeable in the case of the aminophosphines.

There are substantial differences in the rates of reaction of different phosphines. The rate of consumption of phosphine may be slow/fast and rate of production of oxide from the second intermediate may be slow/fast. Therefore the reaction can be over in minutes or weeks.

Further preferred features and embodiments of the present invention will now be described by way of non-limiting examples.

EXAMPLE 1

Materials and Methods

Analysis of Enantiomeric Excesses

The product four coordinated phosphorus compounds were analysed by high performance liquid chromatography on chiral stationary phases (CSP-HPLC). Typically, a 25 μL sample of the reaction mixture was injected onto the HPLC column.

Tert-Butylmethyl(diphenylamino)phosphine oxide ($^t$BuMePNPh$_2$) was analysed on a CHIRALPAK AS-H column 25 cm×0.46 cm I.D., with pentane/ethanol (98:2) as the mobile phase and a flow rate of 0.7 mL/min with the UV detector operating at 254 nm. This gave retention times of 20 and 37 minutes for racemic phosphine oxide.

tert-Butylcyclohexylbenzylphosphine oxide was analysed on a CHIRALPAK AS-H column 25 cm×0.46 cm I.D., with n-heptane/2-propanol (99.5:0.5) as the mobile phase and a flow rate of 0.5 mL/min with the UV detector operating at 235 nm. This gave retention times of 9 and 9.9 minutes for racemic phosphine oxide.

o-Anisylphenylo-tolylphosphine oxide was analysed on a CHIRALPAK AD column 25 cm×0.46 cm I.D., with pentane/ethanol (90:10) as the mobile phase and a flow rate of 0.5 mL/min with the UV detector operating at 235 nm. This gave retention times of 28 and 32 minutes for racemic phosphine oxide.

tert-Butylmethylphenylphosphine oxide was analysed on a CHIRALPAK AD column 25 cm×0.46 cm I.D., with pentane/ethanol (90:10) as the mobile phase and a flow rate of 0.5 mL/min with the UV detector operating at 264 nm. This gave retention times of 15.4 and 17.4 minutes for racemic phosphine oxide.

Phenylmethyl(diisopropylamino)phosphine oxide (PhMePN$^i$Pr$_2$) was analysed on a CHIRALPAK AD column 25 cm×0.46 cm I.D., with pentane/ethanol (98:2) as the mobile phase and a flow rate of 0.8 mL/min with the UV detector operating at 220 nm. This gave retention times of 33 and 50 minutes for racemic phosphine oxide.

Phenylmethyl(diisobutylamino)phosphine oxide (PhMePN$^i$Bu$_2$) was analysed on a CHIRALPAK AS-H column 25 cm×0.46 cm I.D., with pentane/ethanol (99:1) as the mobile phase and a flow rate of 1.0 mL/min with the UV detector operating at 220 nm. This gave retention times of 24 and 38 minutes for racemic phosphine oxide.

Tert-Butylmethyl(dibenzylamino)phosphine oxide ($^t$BuMePN(CH$_2$Ph)$_2$) was analysed on a CHIRALPAK AS-H column 25 cm×0.46 cm I.D., with pentane/ethanol (98:2) as the mobile phase and a flow rate of 0.6 mL/min with the UV detector operating at 254 nm. This gave retention times of 26 and 35 minutes for racemic phosphine oxide.

The analysis of o-anisylmethylphenylphosphine oxide (PAMPO) was determined on a CHIRALPAK AD (Trade Mark) column, 25 cm×0.46 cm I.D with hexane/2-propanol (96:4) as the mobile phase and a flow rate of 1.0 mL/min with the U.V. detector operating at 235 nm. This gave retention times of 42 and 58 minutes for racemic PAMPO. The absolute configuration of PAMPO enantiomers was assigned by comparison to samples of known configuration. A sample of (R)-PAMPO was prepared following the methods of Brown and co-workers (Carey et al., 1993; Brown et al., 1990). The retention times of the racemic sample were compared with that of (R)-PAMPO prepared via this method. The first PAMPO enantiomer peak eluted after 42 minutes was thereby confirmed to be of R-configuration.

Naphthylmethylphenylphosphine oxide (NMPPO) was analysed on a CHIRALPAK OD column, 25 cm×0.46 cm I.D, with hexane/2-propanol (90/10) as the mobile phase and a flow rate of 0.7 mL/min with the U.V. detector operating at 254 nm. This gave retention times of 25 and 28 minutes for racemic NMMPO.

o-Tolylphenylmethylphosphine oxide (PTMPO) was analysised on a CHIRALPAK AD column, 25 cm×0.46 cm I.D., with hexane/2-propanol (96:4) as the mobile phase and a flow rate of 1.0 mL/min with the UV detector operating at 254 nm. This gave retention times of 29 and 47 minutes for racemic PTMPO.

(o-chlorophenyl)phenylmethylphosphine oxide was analysised on a CHIRALPAK AD column, 25 cm×0.46 cm I.D., with hexane/2-propanol (95:5) as the mobile phase and a flow rate of 1.0 mL/min with the UV detector operating at 254 nm. This gave retention times of 39 and 48 minutes for racemic phosphine oxide.

1,2-bis(phenylo-tolylphosphinoyl)ethane (diPTMPO) was analysised on a CHIRALPAK AD column, 25 cm×0.46 cm I.D., with hexane/2-propanol (90:10) as the mobile phase and a flow rate of 1.0 mL/min with the UV detector operating at 254 nm. This gave retention times of 43.9 minutes for the meso diastereomer, slightly overlapped with those for the racemic diastereomer at 47.0 and 54.6 minutes.

Yields were determined using o-anisylmethylphenylphosphine sulfide (PAMPS) or triphenylphosphine sulphide as an internal standards. The other products of the reaction were those expected from Appel conditions namely the alkyl halide and/or alkene elimination products depending on the particular chiral alcohol used.

EXAMPLE 2

Representative Reactions

Representative Procedure A: Using Carbon Tetrachloride as Solvent at Reflux

A 5 mL round bottom flask equipped with stirring bar, reflux condenser and nitrogen inlet/outlet was charged with PAMP (1 equiv, 25 mg, 0.11 mmol), chiral alcohol (1.2 equiv, 0.13 mmol) and carbon tetrachloride (3 mL). The reaction was refluxed for 24 hours. A sample was then directly removed for HPLC analysis.

Representative Procedure B: Using 1 Eqv. Carbon Tetrachloride in Solvent at Reflux A 5 mL round bottom flask equipped with stirring bar, reflux condenser and nitrogen inlet/outlet was charged with PAMP (1 equiv, 25 mg, 0.11 mmol), chiral alcohol (1.2 equiv, 0.13 mmol) and the required solvent (3 mL). The solution was stirred and to this carbon tetrachloride (1 equiv, 9.6 microlitres, 0.11 mmol) was added. The reaction was refluxed and on completion a sample was directly removed for HPLC analysis.

Representative Procedure C: Using Hexachloroacetone (HCA) in Benzene at Room Temperature.

A 5 mL round bottom flask equipped with nitrogen inlet/outlet was charged with PAMP (1 equivalent, 25 mg, 0.11 mmol), chiral alcohol (1.2 equivalents, 20 mg, 0.13 mmol) and solvent (3 mL). The solution was slowly stirred to effect dissolution and to it was added hexachloroacetone (1 equivalent, 16.7 microlitres, 0.11 mmol) via micro syringe. The reaction was stirred at room temperature for 1 week. A sample was removed directly from the reaction solution for HPLC analysis.

Representative Procedure D: Using Hexachloroacetone (HCA) in Toluene at −78° C. with Subsequent Warming.

Dry stock solutions of PAMP (0.109 M), HCA (0.109 M) and alcohol (0.131 M) in toluene were prepared. A set of reaction vessels (20 mL) was dried and to each was added dry toluene (2 mL) followed by dry PAMP stock solution (1 mL) and dry alcohol stock solution (1 mL). The vessels were cooled to −78° C. and allowed to stir for 5 minutes. To each was then added dry HCA stock solution (1 mL) over 2 minutes. The vessels were held at −78° C. for 1 hour, then allowed to warm to room temperature and stirred for 12 hours. A sample was removed directly from the reaction solution for HPLC analysis.

EXAMPLE 3

Effect of Different Chiral Alcohols Using Procedure A

A series of chiral non-racemic terpineols structurally related to menthol was then examined to determine their influence on reaction selectivity. In all cases reactions were performed in carbon tetrachloride at reflux with 1:1 PAMP/alcohol stoichiometry using representative procedure A. The results are shown in Table 1.

TABLE 1

| Entry | Chiral Alcohol | ee (%) | Yield (%) | Configuration of P═O |
|---|---|---|---|---|
| 1 (−) Menthol | | 24 | 65 | R |
| 2 (−) 8-Phenylmenthol | | 53 | 66 | R |
| 3 (−) trans-2-Phenylcyclohexanol | | 19 | 80 | R |

TABLE 1-continued

| Entry | Chiral Alcohol | ee (%) | Yield (%) | Configuration of P=O |
|---|---|---|---|---|
| 4 (+) Fenchyl alcohol | | 23 | 82 | S |
| 1 Fructose derivative | | 16 | 28 | S |
| 2 (1R,2S)-(−)-Cyclohexandiol | | 18 | 68 | R |

EXAMPLE 4

Effect of Amino Alcohols Using Procedure B

A series of alcohols related to (S)-(−)-2-amino-1,1-diphenyl propanol was tested. These included variation of the substituents around both the tertiary alcohol site and around the chiral carbon. The results are shown in Table 2. The solvent used was acetonitrile.

TABLE 2

| Alcohol | Entry | ee % | Yield % | Config. |
|---|---|---|---|---|
| | 1. (S)-(−)-2-amino-1,1-diphenyl propanol | 51 | 64 | R |
| | 2. (S)-(−)-2-amino-3-methyl-1,1-diphenyl-butan-1-ol | 19 | 57 | R |
| | 3. (S)-(−)-2-amino-(1,1,3)-triphenyl-propan-1-ol | 21 | 66 | R |

TABLE 2-continued

| Alcohol | Entry | ee % | Yield % | Config. |
|---|---|---|---|---|
| (structure with Ph, Ph, OH, NH$_2$, Ph) | 4. (R)-(−)-2-amino-(1,1,3)-triphenyl-propan-1-ol | 18 | 69 | S |
| (structure with Ph, Ph, OH, NH$_2$, isobutyl) | 5. (S)-(−)-2-amino-4-methyl-1,1-diphenyl-pentan-1-ol | 26 | 65 | R |

EXAMPLE 5

Use of Hexachoroacetone as the Electrophile

A number of electrophiles have been used. One of these is hexachloroacetone reported in 1979 by Magid and co-workers (Magid et al., 1979). They reported that the conditions required are milder with this reagent than with carbon tetrachloride so that the reactions can be carried out at room temperature and are complete sooner. The system was later applied by Villeneuve and Chan (Villeneuve et al., 1997) for the conversion of carboxylic acids to acid chlorides effected at temperatures as low as −78° C. They also found that addition of half an equivalent of HCA yielded the same product in high yield. With these observations in mind, we attempted to carry out asymmetric phosphine oxidations using PAMP/HCA/alcohol system.

The procedure developed (representative procedure C) involved addition of HCA (1 equiv) to a stirring solution of PAMP (1 equiv) and (−)-menthol (1.2 equivalents) in solvent at room temperature. The reaction was stirred for 1 week. HPLC of the crude reaction material gave a very clean trace and indicated (R)-PAMPO was formed in 26% ee and 94% yield (determined by internal standard). The reaction was repeated with (+)-menthol, confirming enantioselectivity as (S)-PAMPO was produced in 26% ee and similar yield.

The choice of reaction solvent plays an important role in determining selectivity. Table 3 shows the selectivities achieved by varying the solvent and temperature.

TABLE 3

Enantioselectivity of PAMPO on reaction of (−)-menthol with PAMP/HCA in different solvents.[a]

| Entry | Solvent | Temp | ee % |
|---|---|---|---|
| 1 | Benzene | R.T. | 26 |
| 2 | Benzene | 40° C. | 26 |
| 3 | Benzene | 88° C. | 22 |
| 4 | Toluene | R.T. | 24 |
| 5 | HCA | 0° C. | 8 |
| 6 | Acetonitrile | R.T | 4 |
| 7 | Diethyl ether | −78° C.[b] | 6 |

[a]Reactions were carried out generally according to representative procedure C and analysis carried out after reaction overnight;
[b]addition of HCA at −78° C. and reaction allowed to warm to R.T.

The choice of chiral alcohol plays an important role in determining selectivity. Table 4 shows the selectivities achieved by varying the alcohol.

TABLE 4

Enantioselectivity and yield of PAMPO on reaction of different chiral alcohols with PAMP/HCA using Procedure C in benzene as solvent

| Alcohol | Entry | ee % | Yield % | Config. P=O |
|---|---|---|---|---|
| (menthol structure) | 1. (−)-menthol | 26 | 94 | R |
| (8-phenylmenthol structure) | 2. (−)-8-phenylmenthol | 41 | 97 | R |
| (trans-2-phenylcyclohexanol structure) | 3. (−)-trans-2-phenylcyclohexanol | 23 | — | R |

EXAMPLE 6

Use of 1-naphthylmethylphenylphosphine

The generality of the process of the present invention was tested 1-naphthylmethylphenylphosphine (NMPP) and methylphenylo-tolylphosphine (MPTP) substrate with HCA as the electrophile. Table 5 shows results.

TABLE 5

Enantioselectivity of different phosphine oxides produced in the phosphine/HCA/alcohol system.[a]

| Alcohol | Entry | ee % NMPPO | ee % MPTPO |
|---|---|---|---|
|  | 1. (−)-menthol | 29[b] | 51[c] |
|  | 2. (−)-8-phenylmenthol | 24[d] | 48[e] |
|  | 3. (+)-isomenthol | 20[f] | — |

[a]Reactions were carried out according to general procedure C using benzene as solvent and stirred for 1 week at room temperature. The yields of phosphine oxide are quantitative as determined by $^{31}P$ studies.
[b]The second isomer eluted on Chiralcel OD column was in excess
[c]The second isomer eluted on Chiralcel AD column was in excess
[d]The second isomer eluted on Chiralcel OD column was in excess
[e]The second isomer eluted on Chiralcel AD column was in excess
[f]The first isomer eluted on Chiralcel OD column was in excess

EXAMPLE 7

Hexachloroethane (HCE) as the Electrophile

The use of HCE was reported by Appel and Scholer in 1977 (Appel et al., 1977). It has the advantages of simpler procedure and easy handling of the relatively harmless HCE and easy removal of the by-product, tetrachloroethylene. General procedure C, with HCE substituted for HCA, in conjunction with (−)-menthol was used to oxidise methylphenyl-o-tolylphosphine (MPTP) and MPTPO was obtained in 32% ee and 84% yield. The ee was in the second isomer eluted on the AD column.

EXAMPLE 8

N-Chlorosuccinimide (NCS) as the Electrophile

General procedure C, with NCS substituted for HCA, in conjunction with (−)-menthol was used to oxidise methylphenylo-tolylphosphine (MPTP) and MPTPO was obtained in 37% ee and 70% yield. Using 8-phenylmenthol as the chiral alcohol in the oxidation of PAMP, gave PAMPO in 53% ee. The ee was in the second isomer eluted on the AD column.

EXAMPLE 9

Using a Chiral Thiol as Oxidant

A dry 10ml round bottom flask equipped with nitrogen inlet/outlet and activated 4Å molecular sieves was charged with PAMP (1 equivalent, 25mg, 0.11mmol), (+)-neomethanethiol (1.2 equivalents, 22.8mg, 0.132mmol) and benzene (5ml). The solution was stirred and to it was added hexachloroacetone (1 equivalent, 16.7 microliters, 0.11mmol) via microliter syringe. The reaction was stirred at room temperature for 3 days. A sample was removed directly for HPLC analysis. An enantiomeric excess of 12% was obtained in the PAMPS produced. The ee was in the first isomer on the AD column.

EXAMPLE 10

Using a Chiral Diol, and Conversion into Epoxide

A dry 10 ml round bottom flask equipped with nitrogen inlet/outlet and activated 4 Å molecular sieves was charged with PTMP (1 equivalent, 21 mg, 0.098 mmol), (1R,2R)-(−)-1,2-dicyclohexyl-1,2-ethanediol (1.2 equivalents, 27 mg, 0.119 mmol), finely ground potassium carbonate (1 equivalent, 13.5 mg, 0.098 mmol) and benzene (5 ml). The solution was stirred and to it was added hexachloroacetone (1 equivalent, 14.9 microlitres, 0.098 mmol) via microlitre syringe. The reaction was stirred at room temperature for 3 days. A sample was removed directly for HPLC analysis. An enantiomeric excess of 18% was obtained in the PAMPO produced. (R)-PAMPO was in excess.

EXAMPLE 11

Using Diacetone-D-Glucose as the Alcohol

A predried 10 mL round bottom flask equipped with stirring bar and nitrogen inlet/outlet was charged with PAMP (1 equiv, 19.5 mg, 0.085 mmol), diacetone-D-glucose (1.2 equiv, 26.5 mg, 0.102 mmol) and 5 mL of dry benzene was added. Pre-dried 4 Å molecular sieves were charged and the mixture was stirred for 5 minutes, followed by addition of HCA (1 equiv, 13 µL, 0.086 mmol). The reaction was stoppered and stirred overnight at room temperature. Triphenylphosphine sulfide was added as standard and the solution was stirred for 5 minutes. A sample was taken for HPLC analysis. An enantiomeric excess of 2% was obtained in the PAMPO produced and a yield of 47% was obtained. (R)-PAMPO was in excess.

EXAMPLE 12

Using Diacetone-D-Glucose as the Alcohol and Pyridine as an Additive

A predried 10 mL round bottom flask equipped with stirring bar and nitrogen inlet/outlet was charged with PAMP (1 equiv, 21.5 mg, 0.093 mmol), diacetone-D-glucose (1.2 equiv, 29.0 mg, 0.112 mmol) and 5 mL of dry benzene. 4 Å pre-dried molecular sieves were charged and the mixture was stirred for 5 minutes followed by addition of Pyridine (1 equiv, 7.5 µL, 0.093 mmol) and HCA (1 equiv, 14.5 µL, 0.095 mmol). The reaction was stoppered and stirred overnight at room temperature. Triphenylphosphine sulfide was added as standard and the solution was stirred for 5 minutes. A sample was taken for HPLC analysis. An enantiomeric excess of 20% was obtained in the PAMPO produced and a yield of 64% was obtained. (S)-PAMPO was in excess.

EXAMPLE 13

Variation on Reaction C

Methylphenyl-o-tolyl phosphine was reacted with HCA as the electrophile and (−)-menthol as the alcohol according to representative procedure C except: (i) the solvent was toluene; (ii) the concentration of all reagents was five times more; (iii) the reaction was initiated at −78 degrees C. by the addition of the HCA and allowed to warm to room temperature overnight. This gave rise to a waxy solid. Then dry toluene (2 mL) was added and the mixture heated to 50 degrees C. to give a clear solution which was analysed as before. The result was 68% ee and 70% yield. The ee was in the second enantiomer eluted on the AD column.

EXAMPLE 14

Effect of Different Chiral Alcohols Using Procedure D with PAMP

Enantioselectivity of PAMPO produced by reaction of PAMP under Representative Procedure D was recorded for different alcohols. The results are shown in Table 6.

TABLE 6

Enantioselectivity of PAMPO produced by reaction of PAMP under Representative Procedure D.[a]

| Entry | Alcohol | ee % | Configuration |
|---|---|---|---|
| 1 | (−)-menthol | 50 | R |
| 2 | (−)-8-phenylmenthol | 77 | R |
| 3 | (+)-trans-2-tert-butylcyclohexanol | 75 | R |
| 4 | (+)-neomenthol | 64 | S |
| 5 | (+)-isomenthol | 38 | S |
| 6 | (S)-1-Octyn-3-ol | 30 | R |
| 7 | (R)-3-methyl-2-butanol | 27 | R |
| 8 | (S)-1-phenyl-1-butanol | 18 | R |
| 9 | (1R,2R)-2-benzoylcyclohexanol | 8 | S |
| 10 | (−)-isopinocampheol | 6 | S |
| 11 | cholesterol | 6 | S |
| 12 | (1S,2S,5R)-2-isopropyl-1,5-dimethylcyclohexanol[b] | 5 | S |
| 13 | (−)-10-dicyclohexylsulfamoyl-D-isoborneol[c] | 72 | R |

[a]Reactions were carried out generally according to representative procedure D and analysis carried out after reaction overnight; yields are generally quantitative;
[b]at room temperature;
[c]initiated at −30° C.

EXAMPLE 15

Effect of Different Initiation Temperatures Using PAMP in Procedure D

The effect of different initiation temperatures using PAMP in procedure D was investigated. The results are shown in Table 7.

TABLE 7

Enantioselectivity of PAMPO produced by reaction of PAMP under Representative Procedure D but with the initial temperature at which HCA added varied as indicated.[a]

| Alcohol | −78° C. | −50° C. | −30° C. | 25° C. |
|---|---|---|---|---|
| (−)-menthol | 50 | 42 | 41 | 26 |
| (−)-8-phenylmenthol | 77 | 57 | 60 | 41 |
| (+)-trans-2-tert-butylcyclohexanol | 75 | 62 | 60 | — |
| (+)-neomenthol | 64 | 58 | 59 | — |
| (+)-isomenthol | 38 | 36 | 33 | 17 |
| (−)-10-dicyclohexylsulfamoyl-D-isoborneol | 51 | 67 | 72 | 22 |

[a]Reactions were carried out generally according to representative procedure D and analysis carried out after reaction overnight; yields are generally quantitative, product configurations correspond to those in Table 6.

EXAMPLE 16

Effect of Different Solvents Using PAMP in Procedure D

Reaction procedure D was performed in different solvents. The results are shown in Table 8.

TABLE 8

Enantioselectivity of PAMPO produced by reaction of PAMP under Representative Procedure D but with the solvent varied as indicated.[a]

| Alcohol | Toluene | THF | DCM | Ether | Acetonitrile |
|---|---|---|---|---|---|
| (−)-menthol | 50 | 52 | — | 13 | — |
| (−)-8-phenylmenthol | 77 | 63 | 69 | 64 | 66 |
| (+)-trans-2-tert-butylcyclohexanol | 75 | 66 | 70 | 58 | 63 |
| (+)-neomenthol | 64 | 52 | 33 | 26 | 24 |
| (+)-isomenthol | 38 | 41 | 33 | 43 | — |
| (−)-10-dicyclohexylsulfamoyl-D-isoborneol | 51 | 34 | 43 | 4 | 24 |

[a]Reactions were carried out generally according to representative procedure D and analysis carried out after reaction overnight; yields are generally quantitative, product configurations correspond to those in Table 6.

EXAMPLE 17

Effect of Different Concentrations Using PAMP in Procedure D

Application of procedure D but with a reduced amount of solvent such that the overall concentration of PAMP is 0.109 M results in 34% ee in the resultant PAMPO. This may be compared with the normal concentration (0.022 M) which gives 50% ee.

EXAMPLE 18

Use of Different Phosphines and Alcohols in Procedure D

Reaction procedure D was carried out using different phosphines. The results are shown in Table 9.

TABLE 9

Enantioselectivity of phosphine oxides produced from various phosphines by reaction under Representative Procedure D using various alcohols as indicated.[a]

| Phosphine R¹R²R³P | | | (−)-menthol | (−)-8-phenyl menthol | (+)-trans-2-tert-butyl cyclohexanol | (+)-neomenthol |
|---|---|---|---|---|---|---|
| R¹ | R² | R³ | | | | |
| Ph | Me | o-Anisyl | 50 | 77 | 75 | 64 |
| Ph | Me | o-Tolyl | 80 | 75 | 76 | 72 |
| Ph | Me | o-Chloro | 79 | 73 | 74 | 69 |
| Ph | o-Anisyl | o-Tolyl | −32 | −11 | 13 | 22 |
| Ph | Me | tert-Butyl | 52 | — | — | −60[b] |
| tert-Butyl | c-hexyl | benzyl | 45 | 49 | — | — |

[a]Reactions were carried out generally according to representative procedure D and analysis carried out after reaction overnight; yields are generally quantitative, product configurations are mostly undetermined and where negative and positive values are quoted this is to indicate that the opposite enantiomer is in excess; with (+)-isomenthol

EXAMPLE 19

Use of Chiral Non-Racemic Amine in Procedure D with PAMP

Procedure D was applied to PAMP but replacing the alcohol with (−)-α-methylbenzylamine The resultant aminophosphonium salt showed an enantiomeric excess of 12%.

EXAMPLE 20

Use of Aminophosphines

The Enantioselectivity of phosphine oxides produced from various aminophosphines using various alcohols was measured.

The standard reaction procedure was as follows. Stock solutions of phosphine (25 mg/mL, approx. 0.1 M), alcohol (0.118 M) and carbon tetrachloride (0.099) were prepared and stored overnight in previously dried vessels containing 4 Å molecular sieves. A dried reaction vessel was filled with an atmosphere of $N_2$ and dry toluene (2 mL) added to it. This was then followed by the addition of the amino-phosphine solution (1 mL), the alcohol solution (1 mL) and the solution of carbon tetrachloride (1 ml). The reaction was stirred for a total of between 6-8 days at room temperature. At various time intervals, samples were removed and analyzed by HPLC and the results are shown in Table 10.

TABLE 10

Enantioselectivity of phosphine oxides produced from various aminophosphines by reaction using various alcohols as indicated.[a]

Using phenylmethyl(di-isopropylamino)phosphine PhMePN$^i$Pr$_2$

| Time (days) | (+)-menthol | (−)-menthol | Reaction procedure |
|---|---|---|---|
| 1 | +58 | −64 | standard |
| 1 | +57 | −60 | initiation at −55° C., slow warm to r.t. |
| 1 | +68 | −64 | concentration approx. 0.6 M |
| 1 | +74 | −73 | 6 equivalents of CCl$_4$ |
| 8 | +42 | −42 | standard |
| 4 | +38 | −42 | initiation at −55° C., slow warm to r.t. |
| 8 | +46 | −40 | concentration approx. 0.6 M |
| 8 | +52 | −50 | 6 equivalents of CCl$_4$ |

TABLE 10-continued

Enantioselectivity of phosphine oxides produced from various aminophosphines by reaction using various alcohols as indicated.[a]

Using phenylmethyl(di-isobutylamino)phosphine PhMePN$^i$Bu$_2$

| Time (days) | (+)-menthol | (−)-menthol | Reaction procedure |
|---|---|---|---|
| 1 | +47 | −46 | standard |
| 1 | +53 | −54 | initiation at −78° C., slow warm to r.t. |
| 3 | +43 | −44 | standard |
| 3 | +45 | −45 | initiation at −78° C., slow warm to r.t. |
| 6 | +42 | −44 | standard |
| 6 | +45 | −43 | initiation at −78° C., slow warm to r.t. |

| Phosphine | Alcohol | ee | Reaction procedure |
|---|---|---|---|
| PhMePN$^i$Pr$_2$ | (−)-menthol | −64 | standard |
| PhMePN$^i$Pr$_2$ | (−)-8-phenylmenthol | −68 | standard |
| PhMePN$^i$Pr$_2$ | (−)-8-phenylmenthol | −59 | initiation at −78° C., slow warm to r.t. |
| PhMePN$^i$Pr$_2$ | (+)-neomenthol | +17 | standard |
| PhMePN$^i$Bu$_2$ | (−)-menthol | −46 | standard |
| PhMePN$^i$Bu$_2$ | (−)-8-phenylmenthol | −72 | standard |
| $^t$BuMePNPh$_2$ | (−)-menthol | 20 | standard |
| $^t$BuMePNCH$_2$Ph | (−)-menthol | 22 | standard |

[a]Reactions were carried out generally according to the standard procedure, except where noted; analysis carried out after reaction overnight, except where noted; yields are generally quantitative; product configurations are undetermined, + ee values denote that the first enantiomer eluted is in excess, − ee values denote the second eluted enantiomer in excess; in most cases there are a number of side-products produced from the direct reaction of the phosphine with the alcohol.

Four Examples Remain to be Inserted

EXAMPLE 21

Use of Different Chlorine Sources

The enantioselectivity of PAMPO produced from PAMP using different chlorine sources was measured. The results are shown in table 11.

TABLE 11

Enantioselectivity of PAMPO produced by reaction of PAMP under Representative Procedure D but with the chlorine source varied as indicated.[a]

| Alcohol | HCA | HCCA[b] | NCS[c] | HCE[d] | CCl₄ |
|---|---|---|---|---|---|
| (−)-menthol | 50 | 48 | 45 | 40 | 30 |
| (−)-8-phenylmenthol | 77 | 76 | 73 | 50 | 50 |

[a]Reactions were carried out generally according to representative procedure D and analysis carried out after reaction overnight; yields are generally quantitative, product configurations correspond to those in Table 6,
[b]HCCA: 2,3,4,5,6,6-hexachloro-2,4-cyclohexadien-1-one;
[c]N-chlorosuccinimide;
[d]hexachloroethane.

EXAMPLE 22

Application of the Process to a Mixture of Diastereomeric P-Chirogenic Phosphines

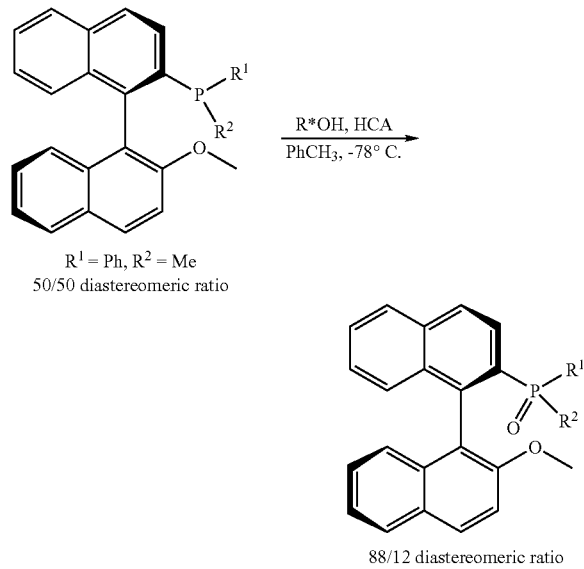

R¹ = Ph, R² = Me
50/50 diastereomeric ratio

88/12 diastereomeric ratio

In a dry reaction vessel (25 mL) was placed dry degassed toluene (1 mL). To this was was added a solution of an equal parts (50:50) mixture of (R,R)- and (R,S)-2-(methylphenylphosphino)-2'-methoxy-1,1'-binaphthyl (0.5 mL of a 0.10 M solution in toluene, 0.05 mmol) and a solution of (−)-menthol (0.5 mL of a 0.12 M solution in toluene, 0.06 mmol). The vessel was then cooled to −78° C. and, after five minutes, treated with a solution of hexachloroacetone (0.5 mL of a 0.1 M solution in toluene, 0.05 mmol). Stirring was continued at this temperature for a further hour followed by warming to room temperature. The reaction was then stirred for 2 weeks until only phosphine oxide signals were present in the $^{31}$P NMR spectrum. The solvent was then removed under reduced pressure and $^{1}$H and $^{31}$P NMR spectra obtained of the crude mixture. In the $^{1}$H spectrum the diagnostic methoxy signals were observed at δ 3.27 and δ 3.73 ppm. These were present in a ratio of 88:12 with the peak at δ 3.27 ppm in excess, corresponding to the (R,R) diastereomer. The $^{31}$P spectrum was also analysed and the oxide peaks were observed at δ 30.81 and δ 31.11 ppm, also in a ratio of 88:12 with the peak at δ 31.11 ppm in excess. No other peaks were observed in the $^{31}$P spectrum. (The peaks for the starting material have chemical shifts of δ −34.74 and −35.13 ppm).

EXAMPLE 23

Conversion of PTMPO to diPTMPO with Improvement of the Selectivity o-Tolylphenylmethylphosphine oxide (PTMPO) was converted to 1,2-bis(phenylo-tolylphosphinoyl)ethane. Subsequent recrystallisation of the reaction mixture provided enantiomerically pure diPTMPO.

Scalemic o-tolylphenylmethylphosphine oxide (81% ee, 111 mg, 0.482 mmol) was dissolved in THF (0.3 mL), treated at 0° C. with lithium diisopropylamide solution (2.0 M in heptane/THF/ethylbenzene, 0.31 mL, 0.62 mmol) and the mixture stirred for 1 hour. Then cupric chloride (78 mg, 0.58 mmol) was added and stirring continued for a further hour at 0° C. After warming to room temperature, the reaction was quenched with concentrated HCl (0.2 mL) and extracted with chloroform. The extracts were washed with aqueous ammonia and with water and dried over magnesium sulfate. After evaporation of the solvent, HPLC analysis of the mixture showed that the minor enantiomer was below the detection limit (ee>98%) and that there was a small amount of meso-compound present (<10%). One recrystallisation from benzene provided pure (>99.9% ee) material (70 mg, 63% yield).

EXAMPLE 24

Effect of Subjecting Scalemic Phosphine to the Process Thereby Improving the Selection Scalemic PAMP (45% ee, R isomer in excess) was subjected to Representative Procedure D using (−)-menthol as the alcohol to give PAMPO (60% ee, quantitative yield).

EXAMPLE 25

Conversion of P-Chirogenic Phosphine Oxides to Various P-Chirogenic Derivatives

Some of the products of the present process are ideal branch points for the synthesis of a large number of other P-chirogenic phosphorus compounds. Thus, for example, those that carry a methyl group attached to phosphorus can be deprotonated at the methyl group with suitable base and subsequently treated with a wide variety of electrophiles. In this way, a modular approach can be envisaged for the generation of libraries of useful phosphorus compounds. By way of exemplification, o-tolylphenylmethylphosphine oxide (PTMPO) and o-anisylphenylmethylphosphine oxide (PAMPO) were so treated with ketone and imine to generate beta-hydroxy and betaamino phosphine oxides respectively:

Rigorously dried enantiomerically pure (S)-o-anisylphenylmethylphosphine oxide ((S)-PAMPO, 0.137 g, 0.56 mmol) was dissolved in dry THF (3 mL), cooled to 0° C., treated under argon with lithium diisopropylamide solution (2.0 M in heptane/THF/ethylbenzene, 0.36 mL, 0.72 mmol) and the mixture stirred for 30 minutes at 0° C. This mixture was then treated at 0° C. with a solution of the N-phenyl imine of fluorenone (0.143 g, 0.56 mmol) in toluene (1.5 mL). The mixture was allowed to warm to room temperature and stirred overnight. The reaction was then quenched with saturated ammonium chloride (1 mL) and the organics extracted into DCM, dried (MgSO₄) and subjected to column chromatography on silica with elution by ethyl acetate/pentane (1:3) to yield (S)-1-(o-anisylphenylphosphinoyl)-2-(N-phenylamino)-2,2-fluorenylideneethane (0.227 g, 80%); $^1$H-nmr (300 MHz, CDCl$_3$): δ ppm 8.17-8.10 (m, 1H), 7.69-6.39 (series of multiplets, 14H), 6.04-6.01 (m, 2H), 3.27 (s 3H), 3.04-2.87 (m 2H); $^{31}$P-nmr (121.4 MHz, CDCl$_3$): δ ppm 30.54; [α]$_D$ (DCM, c 5.65×10$^{-3}$ g/mL)+9.91°.

Rigorously dried enantiomerically pure (S)-o-anisylphenylmethylphosphine oxide (PAMPO, 0.106 g, 0.43 mmol) was dissolved in dry THF (3 mL), cooled to 0° C., treated under argon with lithium diisopropylamide solution (2.0 M in heptane/THF/ethylbenzene, 0.28 mL, 0.56 mmol) and the mixture stirred for 30 minutes at 0° C. This mixture was then treated at 0° C. with a solution of benzophenone (0.078 g, 0.43 mmol) in toluene (1.5 mL). The mixture was allowed to warm to room temperature and stirred overnight. The reaction was then quenched with saturated ammonium chloride (1 mL) and the organics extracted into DCM, dried (MgSO$_4$) and subjected to column chromatography on silica with elution by ethyl acetate/pentane (1:3) to yield (S)-2-(o-anisylphenylphosphinoyl)-1,1-diphenylethanol (0.156 g, 85%); $^1$H-nmr (300 MHz, CDCl$_3$): δ 32.66 ppm; $^{31}$P-nmr (121.4 MHz, CDCl$_3$): δ ppm 8.01-7.95 9m, 1H), 7.61-6.90 (m 15H), 6.64-6.59 (m, 1H), 6.30 (br s, 1H), 3.38 (s, 3H), 3.01 (d, J=10 Hz, 2H); [α]$_D$ (DCM, c 7.3×10$^{-3}$ g/mL)+5.2°.

Rigorously dried enantiomerically pure (first isomer eluted on Chiralpak AS-H with ethanol) o-tolylphenylmethylphosphine oxide (PTMPO, 0.110 g, 0.48 mmol) in dry THF (3 mL), cooled to 0° C., treated under argon with lithium diisopropylamide solution (2.0 M in heptane/THF/ethylbenzene, 0.33 mL, 0.66 mmol) and the mixture stirred for 30 minutes at 0° C. This mixture was then treated at 0° C. with a solution of benzophenone (0.088 g, 0.48 mmol) in toluene (1.5 mL). The mixture was allowed to warm to room temperature and stirred overnight. The reaction was then quenched with saturated ammonium chloride (1 mL) and the organics extracted into DCM, dried (MgSO$_4$) and subjected to column chromatography on silica with elution by ethyl acetate/pentane (1:3) to yield 2-(o-tolylphenylphosphinoyl)-1,1-diphenylethanol (0.168 g, 85%); $^1$H-nmr (300 MHz, CDCl$_3$): δ ppm 7.56-7.00 (series of multiplets, 19H), 3.53-3.37 (m 2H); $^{31}$P-nmr (121.4 MHz, CDCl$_3$): δ ppm 35.53.

Rigorously dried enantiomerically pure (first isomer eluted on Chiralpak AS-H with ethanol) o-tolylphenylmethylphosphine oxide (PTMPO, 0.125 g, 0.54 mmol) in dry THF (3 mL), cooled to 0° C., treated under argon with lithium diisopropylamide solution (2.0 M in heptane/THF/ethylbenzene, 0.38 mL, 0.76 mmol) and the mixture stirred for 30 minutes at 0° C. This mixture was then treated at 0° C. with a solution of N-phenylimine of benzophenone (0.139 g, 0.54 mmol) in toluene (1.5 mL). The mixture was allowed to warm to room temperature and stirred overnight. The reaction was then quenched with saturated ammonium chloride (1 mL) and the organics extracted into DCM, dried (MgSO$_4$) and subjected to column chromatography on silica with elution by ethyl acetate/pentane (1:3) to yield 1-(o-tolylphenylphosphinoyl)-2-(N-phenylamino)-2,2-diphenylethane (0.201 g, 76%); 1H-nmr (300 MHz, CDCl$_3$): δ ppm 7.58-6.81 (series of multiplets, 16H), 6.60-6.55 (m, 1H), 6.40-6.35 (m, 2H), 3.61-3.40 (m, 2H), 2.22 (s, 3H); $^{31}$P-nmr (121.4 MHz, CDCl$_3$): δ ppm 31.45.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

REFERENCES

Ojima, I., Ed., Catalytic Asymmetric Synthesis; 2nd. Edn., Wiley-VCH, 2000
Brunner, H.; Zettlmeier, W. *Handbook of Enantioselective Catalysis*, VCH, Weinheim, 1993 lists many hundreds of chiral phosphines used to date
Knowles, W. S. *J. Chem. Ed.*, 1986, 63, 222
Kagan, H. B. *Bull. Chim. Soc. Fr.*, 1988, 846
Noyori, R. *Chem. Soc. Rev.*, 1989, 18, 187
Horner et al., Pure Appl. Chem., 9, 225 (1964)
Valentine, in Asymmetric Synthesis (Eds. J. D. Morrison and J. W. Scott), Vol. 4, Academic Press, New York, 1984, Chapter 3
Perlikowska, W.; Gouygou, M.; Daran, J-C.; Balavoine, G.; Mikolajczyk, M. *Tetrahedron Lett.*, 2001, 42, 7841-7845
Appel, R.; Halstenberg, M. in *Organophosphorus Regents in Organic Synthesis*
Cadogan, J. I. G., Academic Press, 1979, Chapter 9, pp. 387-431
Appel, R. *Angew. Chem. Int. Ed. Engl.* 1975, 14, 801
Downie, I. M.; Holmes, J. B.; Lee, J. B. *Chemistry and Industry, London,* 1966, 900
Castro, B. Burgada, R. Lavielle, G. Villiéras, J. *Bull. Soc. Chim. France,* 1969, 2770
Castro, B.; Selve, C. *Bull. Soc. Chim. France,* 1971
Kolodiazhnyi, O. I. *Tetrahedron Asymmetry* 1998, 9, 1279
Pietrusiewicz, K. M.; Zablocka, M. *Chem. Rev.* 1994, 94, 1375
Mitsunobu, O. *Synthesis-Stuttgart,* 1981, 1-28
Kolodiazhnyi, O., I. *Tetrahedron Lett.*, 1995, 36, 3921-3924
Carey, J. V.; Barker, M. D.; Brown, J. M.; Russell, M. J. H. *J. Chem. Soc., Perkin Trans.* 1 1993, 831
Brown, J. M.; Carey, J. V.; Russell, M. J. H. *Tetrahedron* 1990, 46, 4877-4886
Magid, M. R.; Fruchey, S.; Johnson, W. L.; Allen, T. G. *J. Org. Chem.* 1979, 44, 359-363
Villeneuve, G. B.; Chan, T. H.; *Tetrahedron Lett.* 1997, 38, 6489-649
Barry, C. N., Evans, S. A., Journal of Organic Chemistry, 1981, 46, 3361-3364
Robinson, P. L., Barry, C. N., Kelly, J. W. Evans, S. A., JACS, 1985, 107, 5210-5219.

The invention claimed is:

1. A process for the stereoselective preparation of a P-chiral four-co-ordinated phosphorus compound selected from a phosphine oxide, the process comprising reacting a first reactant selected from the group consisting of a chiral alcohol, with a second reactant comprising a P-chiral three-co-ordinated phosphorus compound, in the presence of an electrophile.

2. A process for the stereoselective preparation of a P-chiral four-co-ordinated phosphorus compound selected from a phosphine oxide, the process comprising reacting a first reactant selected from the group consisting of a chiral alcohol, with a second reactant comprising a P-chiral three-co-ordinated phosphorus compound, in the presence of an electrophile, and isolating said P-chiral four-co-ordinated phosphorus compound.

3. A process for the stereoselective preparation of a P-chiral three-co-ordinated phosphorus compound, the process comprising the steps of:

(i) stereoselectively preparing a P-chiral four-co-ordinated phosphorus compound selected from a phosphine oxide, said preparation comprising reacting a first reactant selected from the group consisting of a chiral alcohol, with a second reactant comprising a P-chiral three-co-ordinated phosphorus compound, in the presence of an electrophile;

(ii) optionally isolating said P-chiral four-co-ordinated phosphorus compound; and (iii) reducing said P-chiral four-co-ordinated phosphorus compound.

4. A process according to claim 3 wherein the process is repeated more than once in order to improve the enantiomeric excess (ee) of the product P-chiral three-co-ordinated phosphorus compound.

5. A process according to claim 1 wherein the chiral centre resides on the hydroxy carbon of said chiral alcohol.

6. A process according to claim 1 wherein the chiral alcohol has the formula:

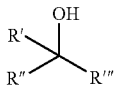

wherein R, R", and R are each independently hydrogen or hydrocarbyl with the proviso that R, R", and R cannot be identical.

7. A process according to claim 1 wherein the alcohol is a cyclic alcohol.

8. A process according to claim 1 wherein two of R, R", and R together with the carbon atom bearing the hydroxyl group form a carbocyclic or heterocycloalkyl ring system.

9. A process according to claim 1 wherein the alcohol is a mono-alcohol.

10. A process according to claim 1 wherein the alcohol is a diol.

11. A process according to claim 1 wherein said chiral alcohol is selected from the group comprising (−)-menthol, (−)-8-phenylmenthol, (−)-trans-2-tert- butylcyclohexanol, (+)-neomenthol, (+)-isomenthol, (S)-1-Octyn-3-ol, (R)-3-methyl-2-butanol, (S)-1-phenyl-1 butanol, (1R,2R)-2-benzoylcyclohexanol, (−)-isopinocampheol, cholesterol, (1S,2S,5R)-2-isopropyl-1,5-dimethylcyclohexanol, (−)-10-dicyclohexylsulfamoyl-D-isoborneol, (−)-trans-2-phenylcyclohexanol, (+)-fenchyl alcohol, (−)-benzenesulfonyl-N-(3,5-dimethylphenypamino-2-borneol, 1,2:4,5-Di-O-isopropylidene-D-fructopyranoside, cyclohexandiol, (S)-(−)-2-amino-1,1-diphenyl propanol, (S)-(−)-2-amino-1,1-diphenyl propanol, (S)-(−)-2-amino-3-methyl-1,1-diphenyl-butan-l-ol, (R)-(+)-2-amino-(1,1,3)-triphenyl-propan-l-ol, (S)-(−)-2-amino-4-methyl-1,1-diphenyl-pentan-l-ol, (−)-trans-2-phenylcyclohexanol, diacetone-D-glucose and (−)-1,2-dicyclohexyl-1,2-ethanediol, or the corresponding enantiomers thereof.

12. A process according to any one of claims 1 to 3 wherein the P-chiral three- co-ordinated phosphorus compound has the formula

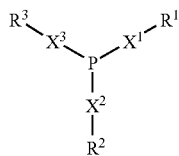

wherein $X^1$, $X^2$ and $X^3$ are each independently $-NR^5$ or absent; and wherein $R^1$, $R^2$, $R^3$ and $R^5$ are each independently hydrogen, halogen, hydrocarbyl or an organometallic group.

13. A process according to claim 12 wherein $X^1$, $X^2$ and $X^3$ are absent.

14. A process according to claim 12 wherein $X^1$ and $X^2$ are absent and $X^3$ is present.

15. A process according to claim 12 wherein $R^1$, $R^2$, $R^3$ and $R^5$ are each independently aryl, heteroaryl, alkyl, carbocycle, heterocycloalkyl, aralkyl or an alkenyl group.

16. A process according claim 12 wherein $R^5$ is an alkyl group.

17. A process according to any one of claims 1 to 3 wherein the stereoselective preparation of said P-chiral four-co-ordinated phosphorus compound occurs in the presence of an electrophile that allows for the formation of a quaternary phosphonium salt and acts as a hydrogen acceptor.

18. A process according to any one of claims 1 to 3 wherein said electrophile is a halogenoalkane.

19. A process according to any one of claims 1 to 3 wherein said electrophile is selected form the group comprising $CX_4$, wherein X is a halogen, hexahaloacetone, hexahaloethane, N-halosuccinimide and trihaloacetonitrile.

20. A process according to claim 19 wherein the halogen is bromine or chlorine.

21. A process according to claim 19 wherein the halogen is chlorine.

22. A process according to any one of claims 1 to 3 wherein said electrophile is selected from the group comprising carbon tetrachloride, hexachloroacetone, hexachloroethane and N-chlorosuccinimide, 2,3,4,5,6,6-hexachloro-2,4-cyclohexadiene-1-one and trichloroacetonitrile.

23. A process according to claim 22 wherein said electrophile is hexachloroacetone.

24. A process according to claim 22 wherein said electrophile is N-chlorosuccinimide.

25. A process according to claim 22 wherein said electrophile is carbon tetrachloride and the P-chiral three-co-ordinated phosphorus compound is as defined claim 14 or 15.

26. A process according to claim 22 wherein said electrophile is hexachloroacetone and the P-chiral three-co-ordinated phosphorus compound is as defined in any one of claims 13, 15 and 16.

27. A process according to any one of claims 1 to 3 wherein said process is performed under Appel, Castro or Evans reaction conditions or a modification thereof.

28. A process according to any one of claims 1 to 3 wherein the second reactant comprising a P-chiral three-co-ordinated phosphorus compound is racemic.

29. A process according to according to any one of claims 1 to 3 wherein the P-chiral three-co-ordinated phosphorus compound is a diastereomeric mixture.

30. A process according to any one of claims 1 to 3 wherein the process is carried out in a solvent.

31. A process according to claim 30 wherein the solvent is aprotic.

32. A process according to claim 30 wherein the solvent is non-polar.

33. A process according to claim 30 wherein the solvent is selected from toluene, THF, dichloromethane, ether and acetonitrile.

34. A process according to claim 33 wherein the solvent is toluene.

35. A process according to claim 33 wherein the solvent is dichloromethane.

36. A process according to claim 33 wherein the solvent is THF.

37. A process according to any of claims 1 to 3 wherein the process comprises the addition of an organic or inorganic base.

38. A process according to any of claims 1 to 3 wherein the process comprises the addition of a metal salt.

39. A process according to any of claims 1 to 3 wherein the process comprises an initiation phase wherein the reaction mixture is initially cooled to below room temperature, and a reaction phase wherein the reaction mixture is heated above the temperature used for the initiation phase.

40. A process according to claim 39 wherein the initiation phase is below 0° C.

41. A process according to claim 39 wherein the initiation phase is below −30° C.

42. A process according to claim 39 wherein the initiation phase is below −50° C.

43. A process according to claim 39 wherein the initiation phase is below −70° C.

44. A process according to claim 39 wherein the initiation phase is about −78° C.

45. A process according to claim 39 wherein the P-chiral three-co-ordinated phosphorus compound is as defined in claim 13.

46. A process according to any of claims 1 to 3 wherein the chiral P-chiral four- co-ordinated phosphorus compound is subsequently converted to a dimeric form creating a mixture of scalemic and meso compounds, and wherein the scalemic compounds are separated from the meso compounds.

47. A process according to claim 46 wherein dimerisation occurs at an alkyl group attached to the phosphorus atom.

48. A process according to claim 47 wherein the alkyl group is a methyl group.

49. A process according to claim 46 wherein the separation is performed by recrystallisation.

50. A process according to claim 46 wherein scalemic chiral P-chiral four-co-ordinated phosphorus compound is o-Tolylphenylmethylphosphine oxide and the dimer is 1,2-bis(phenylo-tolylpho sphinoypethane.

51. A process according to claim 46 wherein scalemic chiral P-chiral four-coordinated phosphorus compound is o-anisylmethylphenylphosphine oxide and the dimer is 1,2-bis(phenyl(2-methoxyphenyl)phosphinoyl)ethane.

52. A process according to claim 46 wherein the dimer is reduced to the corresponding bis-phosphine.

53. A process according to claim 52 wherein the dimer is reduced to generate 1,2-bis(phenyl(2-methylphenyl)phosphino)ethane.

54. A process according claim 52 wherein the dimer is reduced to generate ethane- 1,2-diylbis[(2-methoxyphenyl)phenylphosphane].

* * * * *